(12) United States Patent
Schermer et al.

(10) Patent No.: US 6,756,232 B1
(45) Date of Patent: Jun. 29, 2004

(54) METHOD AND APPARATUS FOR PRODUCING COMPACT MICROARRAYS

(75) Inventors: Mack J. Schermer, Belmont, MA (US); C. Brian Candiloro, Waltham, MA (US); Paul E. Glynn, Braintree, MA (US)

(73) Assignee: PerkinElmer LAS, Inc., Boston, MA (US)

( * ) Notice: Subject to any disclaimer, the term of this patent is extended or adjusted under 35 U.S.C. 154(b) by 0 days.

(21) Appl. No.: 09/527,893

(22) Filed: Mar. 20, 2000

(51) Int. Cl.[7] ................................................. G01N 1/10
(52) U.S. Cl. ........................ 436/180; 436/174; 436/179; 436/180; 422/99; 422/100

(58) Field of Search .......................... 422/99, 100, 103, 422/104; 436/174, 178, 179, 180; 73/863, 863.31, 864, 864.01, 864.11

(56) References Cited

U.S. PATENT DOCUMENTS 5,133,664 A * 7/1992 Hawk et al. .................. 434/115

* cited by examiner

Primary Examiner—Lyle A. Alexander
Assistant Examiner—Dwayne K Handy
(74) Attorney, Agent, or Firm—Hale and Dorr LLP

(57) ABSTRACT

The disclosed pin-lifter can selectively lift pins partially out of a printhead of a spotting instrument and thereby prevent the lifted pins from contacting the substrate during any printing. Methods of using pin-lifters to increase the rate of production of compact microarrays are disclosed.

27 Claims, 13 Drawing Sheets

METHOD AND APPARATUS FOR PRODUCING COMPACT MICROARRAYS

BACKGROUND OF THE INVENTION

The present invention relates to a method and apparatus for producing microarrays. More specifically, the present invention relates to a method and apparatus for increasing the speed of production of compact microarrays.

As is well known (and described for example in U.S. Pat. No. 5,807,522 to Brown et al. and in "DNA Microarrays: A Practical Approach", Schena, Mark, New York, Oxford University Press,1999, ISBN 0-19-963776-8), microarrays are arrays of very small samples of purified DNA or protein target material arranged as a grid of hundreds or thousands of small spots on a solid substrate. When the microarray is exposed to selected probe material, the probe material selectively binds to the target spots only where complementary bonding sites occur, through a process called hybridization. Subsequent quantitative scanning in a fluorescent microarray scanner may be used to produce a pixel map of fluorescent intensities (See, e.g., U.S. Pat. No. 5,895,915, to DeWeerd et al.). This fluorescent intensity map can then be analyzed by special purpose quantitation algorithms which reveal the relative concentrations of the fluorescent probes and hence the level of gene expression, protein concentration, etc., present in the cells from which the probe samples were extracted.

The microarray substrate is generally made of glass which has been treated chemically to provide for molecular attachment of the spot samples of microarray target material. The microarray substrate is also generally of the same size and shape as a standard microscope slide, about 25 mm×75 mm×1 mm thick. The array area can extend to within about 1.5 mm of the edges of the substrate, or can be smaller. The spots of target material (typically DNA) are approximately round. The spot diameter is generally determined by the dispensing or spotting technique used and typically varies from about 75 microns to about 500 microns, and may be as small as about 20 microns. The general trend is toward smaller spots, which produce more compact arrays. The center-to-center spacing between the spots usually falls into the range of 1.5 to 2.5 spot diameters.

FIG. 1A, which is not drawn to scale, shows a top view of a prior art microarray 100. In FIG. 1A, each of the circles represents a tiny spot of target material that has been deposited onto a rectangular glass substrate 101, and the spots are shown in a magnified view as compared to the substrate 101. Assuming typical dimensions of 100 $\mu$m spot diameter and 200 $\mu$m centerto-center spacing between the spots, the illustrated six by six array of spots covers only a 1100 $\mu$m by 1100 $\mu$m square area of the 25 mm by 75 mm area defined by the substrate 101. Thousands of spots are usually deposited in a typical microarray and the spots may cover nearly the entire substrate. The portion of the microarray that is covered with spots of target material may be referred to as the "active area" of the microarray.

There are several well known methods of depositing the spots onto the substrate of a microarray, and instruments that deposit the spots are typically referred to as "spotting instruments". One popular method is to use one or more "pins" to transfer the target material from a reservoir onto the microarray substrate. FIG. 1B shows an example of such a prior art pin 102, which includes a pin head 104 and a needle 106. Both the pin head 104 and the needle 106 are generally cylindrical, and the pin head 104 and needle 106 are generally disposed so that they are coaxial. The diameter of the pin head 104 is greater than the diameter of the needle 106, and the needle is substantially longer than the pin. One end 107 of the needle 106 is tapered or sharpened, and the other end of the needle is attached or bonded to the pin head 104. Examples of such pins are described in, for example, U.S. Pat. Nos. 5,770,151 (Roach et al.) and U.S. Pat. No. 5,807,522 (Brown et al.).

In operation, the sharp ends 107 of the pins are dipped into a reservoir of the liquid target material so that some of the material is "picked up" or becomes attached to the pins. The sharp ends of the pins are then placed in contact with the substrate to deposit tiny amounts of the material onto selected locations of the substrate. The pins are normally moved by a mechanical or robotic apparatus so the spots may be accurately placed at desired locations on the substrate.

Some types of pins are capable of absorbing only enough target material to form a single spot on the microarray before they need to be re-dipped in the reservoir, whereas others can absorb eriough target material from the reservoir to form several or even hundreds of spots before they need to be re-dipped in the reservoir. In either case, the pins must be manufactured to very precise tolerances to insure that each spot formed by the pin will be of controlled size. As a result of these demanding specifications, the pins are rather expensive (e.g., a single pin typically costs several hundred dollars). Also, the sharp ends of the pins are so small and precisely shaped (e.g., a square tip measuring 50 microns on a side) that the pins are fragile. Accordingly, to prevent damage, the sharp ends of the pins must only be exposed to a tiny force when the sharp ends are placed in contact with the substrate or any other solid object.

Spotting instruments typically form microarrays in batches. For example, in a single "run", a spotting instrument may form up to 100 identical microarrays. After forming enough spots to complete the batch of microarrays being spotted, the pins generally need to be washed (to remove any excess liquid target material), and then dried before they can be dipped into another reservoir of target material. So the process of forming microarrays with a "pin-type" spotting instrument includes steps of (1) positioning a pin over a reservoir of target material; (2) dipping the sharp end of the pin into the reservoir; (3) withdrawing the sharp end of the pin from the reservoir; (4) moving the pin over a selected location within the active area of a microarray; (5) lowering the pin to bring the sharp end of the pin into contact with the microarray substrate to form a single spot of controlled size at the selected location; (6) raising the pin to separate the sharp end of the pin from the substrate; (7) repeating steps (4), (5), and (6) until the pin's supply of target material is exhausted or until the desired number of spots have been placed on the bach of microarrays being produced; (8) washing the pin by either placing the pin in a stream of cleaning solution or by dipping the pin into a reservoir of cleaning solution; and (9) drying the pin. The spotting instrument repeats all of these steps numerous times to form a single microarray.

Since microarrays typically include thousands of spots, using only a single pin to form the microarray would be extremely time consuming. Accordingly, spotting instruments are often capable of simultaneously manipulating several pins. FIGS. 1C, 1D and 1E show side, top, and perspective, views respectively of a printhead 110 that can simultaneously hold sixteen pins 102. Printhead 110 is a solid block of material, typically metal, that defines an array of sixteen apertures 112. The apertures 112 are slightly larger than the outer diameter of the needles 106 so the needles can extend through the apertures 112. The apertures 112 are also smaller than the outer diameter of the pin heads 104 so that when the needle of a pin is dropped into one of the apertures 112, the pin head 104 will be supported by the upper surface of the printhead 110. The pins are thereby "slip-fit" into the apertures of the printhead. FIGS. 1F and 1G show side and top views, respectively, of sixteen pins mounted into printhead 110.

FIG. 1H illustrates printhead 110 being lowered to place the sharp ends of the pins 102 into contact with substrate 101 and thereby simultaneously forming sixteen spots of target material on the substrate. As shown, the printhead is generally lowered about 1 mm further than required to place the sharp ends of the pins in contact with the substrate. The slip-fit allows the upper surface of the printhead to be lowered beneath the bottom of the pin heads without imparting significant force to the sharp ends of the pins. The printhead is preferably lowered sufficiently slowly so that the force applied to the sharp ends of the pins (1) is principally determined by the weight of the pin plus a minor additional force due to the friction of the slip-fit and (2) is not significantly affected by inertial forces. The act of lowering the printhead to place the sharp ends of the pins in contact with the substrate and thereby forming spots on the microarray is commonly referred to as "printing".

Commercially available printheads provide between 4 and 72 apertures, thereby accommodating between 4 and 72 pins. Commercially available reservoirs provide a plurality of wells, or individual reservoirs, and permit each pin mounted in a printhead to be dipped into a separate well. Two popular reservoirs useful for producing microarrays are the "96-well plate" and the "384-well plate". Each of these plates provide a rectangular array of wells, each well being capable of holding a unique sample of liquid target material. FIG. 1I shows a top view of a 96-well plate. In 96-well plates, the centers of the individual reservoirs are separated by 9.0 mm, and in 384-well plates, the centers of the individual reservoirs are separated by 4.5 mm. The centers of adjacent apertures in commercially available printheads are correspondingly separated by either 9.0 or 4.5 mm. Pin-type spotting instruments generally include mechanisms for holding or manipulating one or more plates (e.g., either 96-well or 384-well), a printhead, a robotic manipulator for controlling the movement of the printhead, mechanisms for holding a plurality of substrates, a pin washer, and a dryer.

FIGS. 2A and 2B illustrate some of the steps in forming a microarray 200 with a pin-type spotting instrument. Microarray 200 has a rectangular substrate 101 measuring 75 mm by 25 mm and a rectangular active area 202 (within which all spots will be deposited) measuring 18 mm by 54 mm. FIG. 2A shows a rectangular area 210 within which 48 spots have been deposited using a printhead carrying 48 pins. The area within which the 48 spots have been placed is called the "footprint" 210 of the printhead. A 48-pin printhead, carrying four rows of pins with twelve pins in each row, in which the centers of the pins are spaced apart by 4.5 mm, has a rectangular "footprint" that measures 13.5 mm by 49.5 mm, where the "footprint" is the minimum (regularly-shaped, contiguous) area that contains all the spots made by allowing all the pins in the printhead to contact the substrate once. In other words, every single printing deposits 48 spots of target material onto the substrate and those 48 spots fit into a rectangular 13.5 mm by 49.5 mm footprint.

FIG. 2A shows a top view of the footprint 210 of such a printhead superposed onto substrate 101. Footprint 210 represents an area within which 48 spots have been printed onto the substrate 101 of a microarray. Since each spot has a diameter of only about 20 to 500 microns, and since footprint 210 includes only 48 spots, most of the footprint 210 is occupied by empty space (i.e., most of the area of the footprint 210 is not occupied by spots of target material). The microarray is created by repeatedly printing spots onto the substrate with the footprint of each printing being slightly offset (and mostly overlapping) with the footprints associated with all the other printings. FIG. 2B shows the footprint 212 of a second printing. The combined areas of the two footprints 210, 212 will contain 96 spots: two arrays of 48 spots with each array being slightly offset from the other. The microarray is created by repeatedly printing arrays of spots until all desired spots have been placed on the substrate. Normally, the active area of the microarray is filled in until any additional printings would form spots that overlie or otherwise disturb spots from previous printings. The active area generated by the above-discussed 48-pin printhead is typically 18 mm by 54 mm.

One obvious advantage of using multiple pins, is that it reduces the number of printing steps, and therefore the time, required to produce a microarray. However, one disadvantage of using multiple pins is that it increases the difficulty of making a "compact" microarray. For example, as shown in FIGS. 2A and 2B, the active area of the microarray (i.e., the area that contains all the spots) must be at least as large as the printhead's footprint. Since the size of the footprint increases with the addition of more pins, increasing the number of pins used tends to increase the overall size of the active area of the microarray.

Decreasing the active area of a microarray, or making the microarray more "compact", has several advantages. First, the hybridization reaction requires less fluorescently labeled probe material if the active area of the microarray is small, and the probe material is expensive and technically difficult to make in large volumes. Second, the hybridization reaction is more likely to be uniform in rate and extent over a smaller array area than over a large area, producing results of higher quality. Third, subsequent to hybridization, the microarrays are normally scanned for quantitative fluorescence intensity. The output of this scanning process is image files, at least two files per microarray, each file typically of several megabytes. These image files are used as inputs to microarray quantification software programs, which extract numerical results from them. More compact arrays produce smaller image files, easing the downstream data storage and image quantification processes. The relative importance of each of these factors varies from application to application, and experiment to experiment.

By way of example, one useful "compact" microarray configuration has an active area that is an 18 mm square, and 20,000 spots of 80 μm diameter on 127 μm spacing are deposited in that active area. With pins spaced apart from one another by 4.5 mm, a maximum of 16 pins can be used to fabricate such an array. The addition of even a single extra (seventeenth) pin would increase the active area beyond the desired 18 mm square. If each printing takes about a minute (where the time for each printing includes dipping the pins in the target material, contacting the pins to the substrate, and washing and drying the pins), then fabricating such an array with 16 pins will require about 21 hours (1250 separate printings of the sixteen pins are required to product 20,000 spots). Using 32 pins to fabricate the array would reduce the fabrication time in half, but would also double the footprint of the printhead and thereby double the active area of the array.

On one hand, the desire to increase the throughput of the spotting instrument suggests increasing the number of pins in the printhead to provide a high degree of parallelism in the spotting operation. On the other hand, a large number of pins in the printhead forces the microarray's active area to be at least as large as the footprint of the pattern of pins, regardless of how many spots are in the microarray. Because the quality of the results of a microarray experiment are generally judged to be more important than the throughput, the desire for a compact array for improved control of the hybridization reaction normally dominates the decision of how many pins to use. As a result, spotting instruments are often used with less than fully populated printheads. For example, since the above-described type of array can only be printed with a maximum of sixteen pins, even if a printhead of a particular spotting instrument could accommodate 48 pins (i.e., the printhead defines 48 apertures), only 16 pins could be used and the remaining capacity to hold an additional 32 pins would be unused. So, the potential gains in throughput and productivity enabled by a high pin count often remain unrealized due to the problem of the resulting arrays being undesirably large.

It would therefore be advantageous to provide methods and systems for using large numbers of pins to produce compact microarrays.

SUMMARY OF THE INVENTION

These and other objects are provided by a pin-lifter that can selectively lift one or more pins partially out of a printhead and thereby prevent the lifted pins from contacting the substrate during any printing operation. The ability to prevent selected pins from contacting the substrate during a printing (i.e., the ability to selectively disable the printing function of selected pins) can be used, for example, to advantageously increase the rate of production of compact microarrays.

Still other objects and advantages of the present invention will become readily apparent to those skilled in the art from the following detailed description wherein several embodiments are shown and described, simply by way of illustration of the best mode of the invention. As will be realized, the invention is capable of other and different embodiments, and its several details are capable of modifications in various respects, all without departing from the invention. Accordingly, the drawings and description are to be regarded as illustrative in nature, and not in a restrictive or limiting sense, with the scope of the application being indicated in the claims.

BRIEF DESCRIPTION OF THE FIGURES

For a fuller understanding of the nature and objects of the present invention, reference should be made to the following detailed description taken in connection with the accompanying drawings in which the same reference numerals are used to indicate the same or similar parts wherein.

DETAILED DESCRIPTION OF THE PREFERRED EMBODIMENTS

Figure 3D:
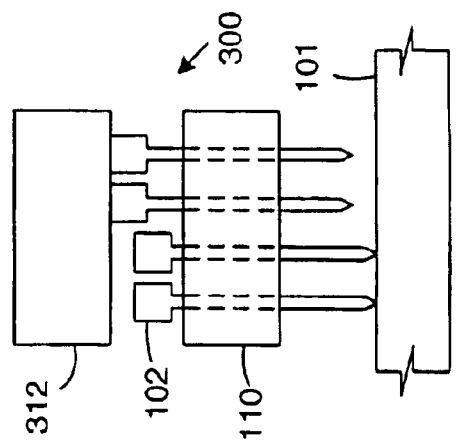
FIG. 3D shows a side view of the configuration shown in FIG. 3C during a printing in which the pin-lifter prevents eight pins from contacting the substrate.
Figure 3C:
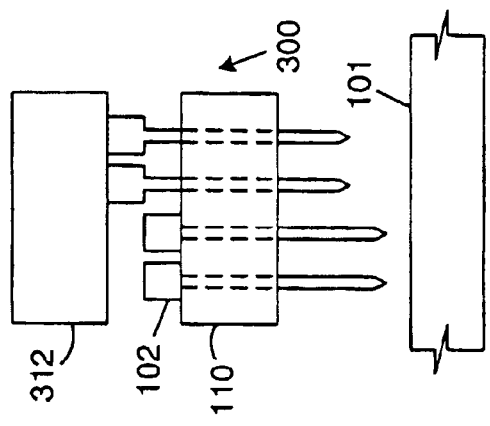
FIG. 3C shows a side view of the configuration of FIG. 3B in which the pin-lifter has lifted eight pins partially out of the printhead.
Figure 3A:
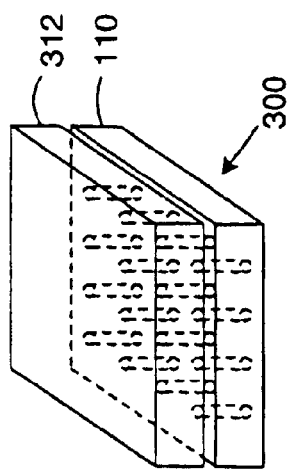
FIG. 3A shows a perspective view of a pin-lifter constructed according to the invention disposed over a printhead.
Figure 3B:
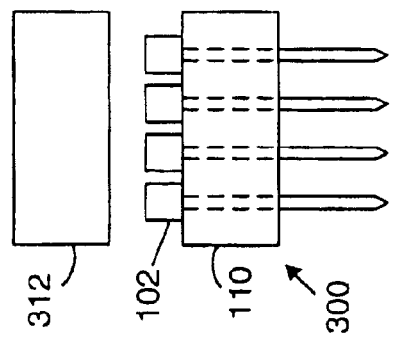
FIG. 3B shows a side view of the pin-lifter shown in FIG. 3A disposed over a printhead in which 16 pins have been mounted.

FIG. 3A shows a perspective view of a portion 300 of a spotting instrument constructed according to the present invention. Portion 300 includes a printhead 110 and a pin-lifter 312 disposed over the printhead 110. FIG. 3B shows a side view of portion 300 when sixteen pins 102 have been mounted in the printhead 110. Pin-lifter 312 is capable of selectively lifting pins partially out of printhead 110. For example, FIG. 3C shows pin-lifter 312 lifting eight of the sixteen pins (i.e., two rows of four pins each) partially out of printhead 110 while portion 300 is disposed over a substrate 101 of a microarray. FIG. 3D shows an example of how pin-lifter 312 can be used to prevent selected pins 102 from printing onto the substrate 101. In FIG. 3D, portion 300 has been lowered relative to substrate 101 (as compared with the position shown in FIG. 3C) to effect a printing (i.e., to bring the sharp ends of some of the pins into contact with the substrate). If pin-lifter 312 was not present (or inactive), positioning the printhead 110 relative to the substrate 101 as shown in FIG. 3D would result in printing sixteen spots of target material onto the substrate 101. However, since pin-lifter 312 has lifted eight of the pins partially out of the printhead, only eight of the pins actually contact the surface of the substrate 101 and only eight spots are printed.

Figure 1A:
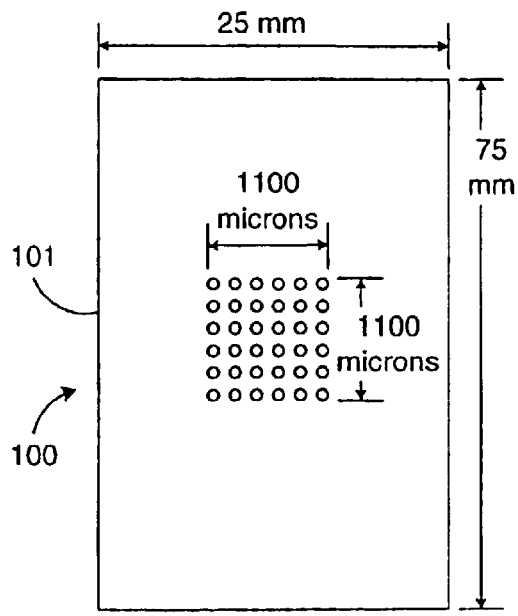
FIG. 1A shows a top view of a prior art microarray.
Figure 1B:
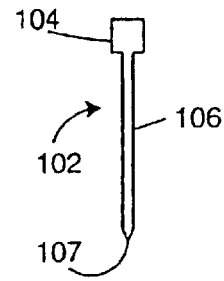
FIG. 1B shows a side view of a prior art pin.
Figure 1C:
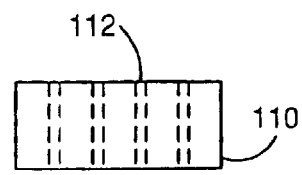
FIGS. 1C, 1D, and 1E show side, top, and perspective views, respectively, of a prior art printhead.
Figure 1D:
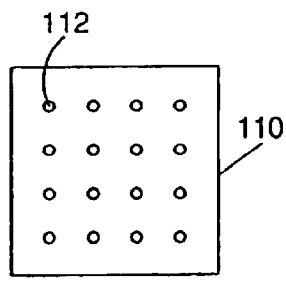
Figure 1E:
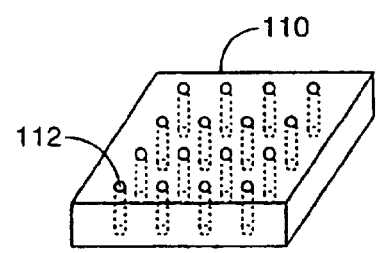
Figure 1F:
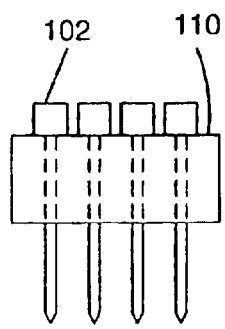
FIGS. 1F and 1G show side and top views, respectively, of sixteen pins mounted in the printhead shown in FIGS. 1C, 1D, and 1E.
Figure 1G:
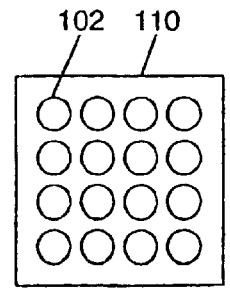
Figure 1H:
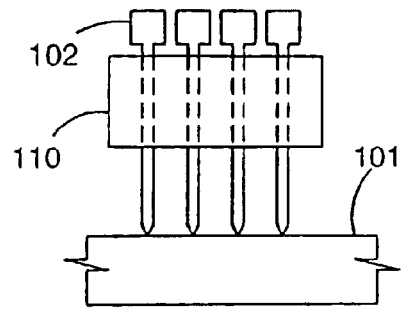
FIG. 1H shows a printing in which the printhead shown in FIG. 1F is lowered sufficiently with respect to a substrate to bring the sixteen pins shown in FIG. 1F into contact with the substrate and thereby form 16 spots of a microarray.
Figure 1I:
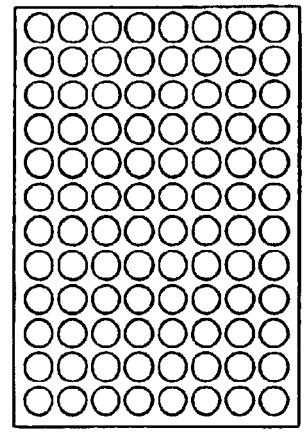
FIG. 1I shows a top view of a prior art 96-well plate.
Figure 2A:
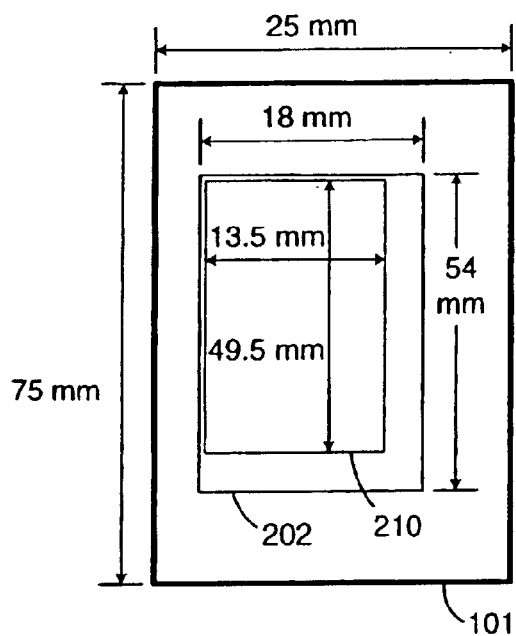
FIGS. 2A and 2B show top views of the footprints associated with two printings.
Figure 2B:
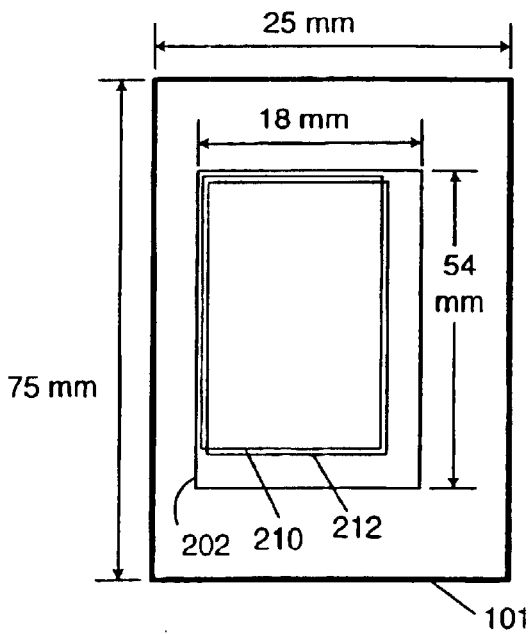

As discussed above in connection with FIG. 1H, printheads are normally lowered about 1 mm further than required to contact the sharp ends of the pins to the surface of the substrate. The amount that the printhead is lowered beyond what is required to bring the sharp ends of the pins into contact with the surface of the substrate may be referred to as the amount of "over-travel". To prevent a particular pin from printing, the pin-lifter 312 lifts the pin by an amount greater than the amount of over-travel used for any particular printing (as shown for example in FIG. 3D). Since most spotting instruments usually use about 1 m of over-travel, it is useful for the pin-lifter to be capable of lifting pins about 2 mm out of the printhead.

Figure 4A:
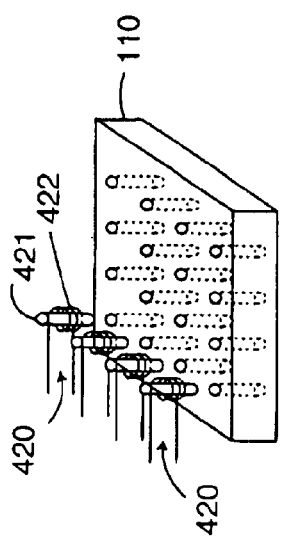
FIG. 4A shows a perspective view of one embodiment of a pin-lifter constructed according to the invention disposed over a printhead.
Figure 4B:
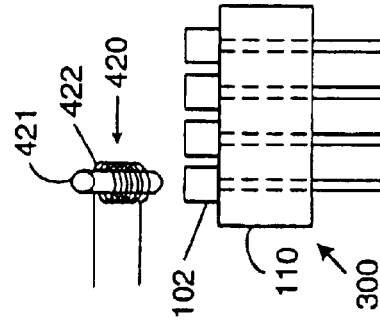
FIG. 4B shows a side view of the pin-lifter shown in FIG. 4A disposed over a printhead in which 16 pins have been mounted.

Some particular embodiments of pin-lifters constructed according to the invention will now be described. After those embodiments have been described, methods of using pin-lifters in accordance with the invention will then be described. FIGS. 4A and 4B show perspective and side views, respectively, of four pin-lifters 420 disposed above four apertures of a sixteen aperture printhead 110. Each of the pin-lifters 420 includes an electromagnet formed from a cylindrical core 421 of "soft" ferromagnetic metal (e.g., nickel-iron) and a coil of wire 422 that is wound around the core 421. Application of an electric current to coil 422 (e.g., DC current) causes the pin-lifter 420 to generate an electromagnetic force. Since most all commercially available pins are fabricated from ferromagnetic material (e.g., pins sold by Telechem are made of 400-series stainless steel), this electromagnetic force can attract the pins and thereby lift them partially out of the printhead. In one preferred embodiment, core 421 is fabricated from Carpenter 49 nickel-iron, and the coil 422 is fabricated from magnet wire.

Figure 4C:
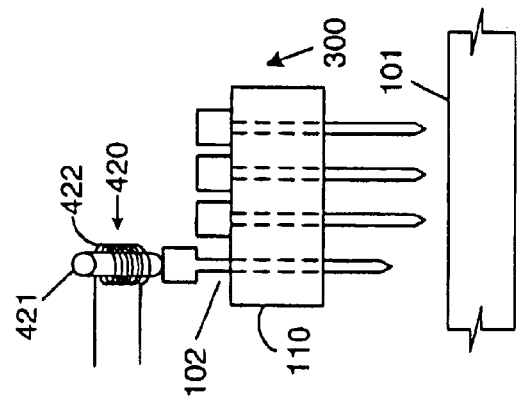
FIG. 4C shows a side view of the configuration shown in FIG. 4B in which the pin-lifters have lifted four pins partially out of the printhead.
Figure 4D:
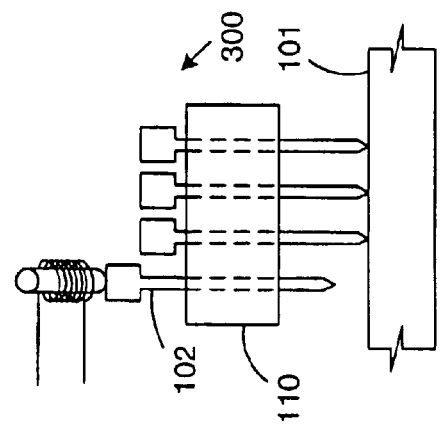
FIG. 4D shows a side view of the configuration shown in FIG. 4C during a printing in which the pin-lifters prevent four pins from contacting the substrate.

FIG. 4A shows a side view of four pin-lifters 420 disposed over the left most row of pins 102 in printhead 110 before application of electric current to the coils. FIG. 4C shows the same pin-lifters 420 after application of electric current to all the coils 422. The electromagnetic force generated by pin-lifters 420 in response to application of the electric current lifts the pins disposed directly beneath the pin-lifters out of the printhead and brings the pins into contact with the cores 421. FIG. 4D illustrates a printing in which only twelve of the sixteen pins in printhead 110 are allowed to contact substrate 110 because the four pin-lifters 420 have prevented the remaining four pins from contacting the substrate.

Each of the pin-lifters 420 is capable of lifting a single pin out of the printhead. Although only four pin-lifters 420 are illustrated in FIGS. 4A–4D, in general, one pin-lifter 420 would normally be provided for every aperture of the printhead (so, e.g., 48 pin-lifters 420 would be disposed over the apertures of a 48 aperture printhead, each of the pin-lifters corresponding to a single one of the apertures). If a pin is present in an aperture, the electromagnetic force generated by application of electric current to the pin-lifter 420 disposed over that pin lifts the pin partially out of the printhead and brings the pin into contact with the core 421. Also, removing the electric current from coil 422 interrupts the electromagnetic force and allows the pin to drop back into a printing position within the printhead.

The cores 421 of the pin-lifters are preferably positioned coaxially over their corresponding apertures in the printhead. Each core 421 directs the magnetic force generated by its pin-lifter down to the pin disposed directly beneath the pin-lifter (i.e., to the pin mounted within the aperture that is coaxial with the core). So, each pin-lifter 420, when actuated by application of electric current, generates a force that lifts the pin disposed directly beneath the pin-lifter. The direction of any attractive force between a pin-lifter 420 and a pin that is not disposed coaxially beneath the pin-lifter's core would not be coaxial with the aperture within which the pin is mounted. Accordingly, friction tends to prevent pin-lifters 420 from attracting pins that are not disposed in apertures coaxial with the pin-lifter's core.

The magnetic force required to hold a pin in contact with core 421 is significantly less than the force required to attract the pin across the air gap (i.e., the force required to cause the pin to move from a printing position within the printhead, as shown in FIG. 4B, to a position in which the pin head is in contact with the core 421, as shown in FIG. 4C). Accordingly, to minimize electric current and heat dissipation requirements associated with lifting a pin, it may be advantageous to initially apply a relatively large pulse of current (to generate a sufficiently large electromagnetic force to attract the pin across the air gap) and thereafter apply only a reduced current (to generate a reduced magnetic force sufficient to hold the pin in contact with the core). Also, since the pins will typically exhibit magnetic hysteresis, it may be advantageous to reverse the direction of current applied to the coil every time the pin-lifter is actuated. In other embodiments, it may be beneficial to lower the pin-lifters 420 so that the cores 421 are in physical contact with the pin heads before applying the electric current to coil 422. After application of electric current, the pin-lifters 420 may then be raised above the printhead, for example to the position shown in FIG. 4C, to lift the pins out of the printhead.

Figure 4F:
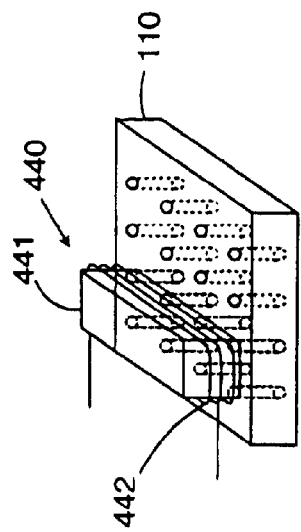
FIGS. 4E and 4F show perspective views of two additional embodiments of pin-lifters constructed according to the invention disposed over a printhead.
Figure 4E:
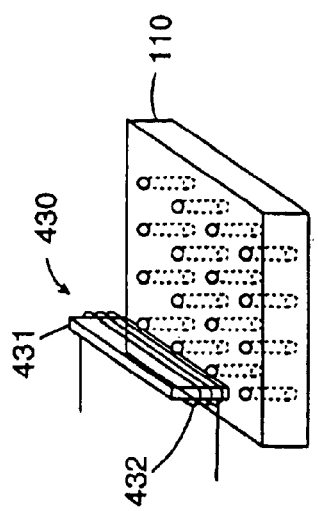

FIG. 4E shows a perspective view of another pin-lifter 430 constructed according to the invention disposed over printhead 110. As with pin-lifter 420, pin-lifter 430 includes a core 431 of "soft" ferromagnetic metal and a coil of wire 432 that is wound around the core 431. However, rather than using a cylindrical core (such as core 421), the core 431 of pin-lifter 430 is rectangular or oblong. More specifically, the core 431 is long enough to cover an entire row of apertures in the printhead. Whereas pin-lifter 420 lifted only a single pin, pin-lifter 430 is capable of simultaneously lifting an entire row of pins. More specifically, application of electric current to coil 432 will lift any pins mounted in the row of apertures directly beneath pin-lifter 430. Although only one pin-lifter 430 is shown in FIG. 4E, it will be appreciated that normally one pin-lifter 430 would be provided for every row of apertures in the printhead. Alternatively, two or more pin-lifters 430 could be used to cover a single row (e.g., four pin-lifters 430, each long enough to cover three apertures, could be used to cover a single row of twelve apertures in a printhead).

The magnetic field generated by approximately 100 ampere-turns is sufficient for pin-lifter 430 to lift the pins disposed beneath it across an air gap at least as large as 2 mm. After the pins have been lifted and are in contact with the core 431, a holding current of no more than 10% of that required to generate the lifting force is sufficient to retain the pins securely. In one preferred embodiment, the core 431 is rectangular and measures 3 mm by 18 mm, the coil 432 is wound 200 times around the core 431, 0.5 amperes are applied to the coil 432 to lift the pins across the air gap, and 0.05 amperes are applied to the coil 432 as a holding current to hold the pins in contact with the core 431 after they have been lifted across the air gap.

FIG. 4F illustrates yet another embodiment of a pin-lifter 440 constructed according to the invention. Pin-lifter 440 includes a core 441 and a coil of wire 442 wound around the core 441. In pin-lifter 440 the core is sufficiently large to cover two rows of the apertures of printhead 110. Application of electric current to coil 442 will lift all pins mounted in the eight apertures disposed directly beneath the core 441. It will be appreciated that core 441 can be sized to cover two or more rows of apertures of any printhead, or, alternatively, the core 441 can be sized to cover portions of multiple rows of apertures. For example, core 441 could be sized to cover all sixteen apertures of printhead 110, so a single pin-lifter 440 could lift all sixteen pins out of printhead 110. As another example, the core 441 of a pin-lifter 440 could be configured to cover four rows of apertures with three apertures per row (i.e., a 4×3 array of twelve apertures). Four such pin-lifters could be used to cover all the apertures of a 48 aperture printhead (i.e., a printhead having four rows with twelve apertures in each row). A configuration of four such pin-lifters could lift all 48 pins out of the printhead, or could selectively lift groups of twelve pins out of the printhead.

An array of single-pin pin-lifters 420 (i.e., one pin-lifter 420 for each aperture of a printhead), advantageously provides independent control over each pin in the printhead. Such control could be considered "random access", since any pin in the printhead could be lifted, or lowered, independently from all other pins. Random access control is advantageous because it provides a high degree of flexibility. However, although multiple-pin pin-lifters 430 and 440 do not provide random access control over every pin in the printhead, the control circuitry for controlling an array of multiple-pin pin-lifters 430, 440 is generally less complex than the control circuitry for controlling an array of single-pin pin-lifters 420 (i.e., because fewer independent elements need to be controlled). Also, an array of multiple-pin pin-lifters is generally less mechanically complex than an array of single-pin pin-lifters (i.e., assuming that both arrays cover the same number of pins).

Figure 4I:
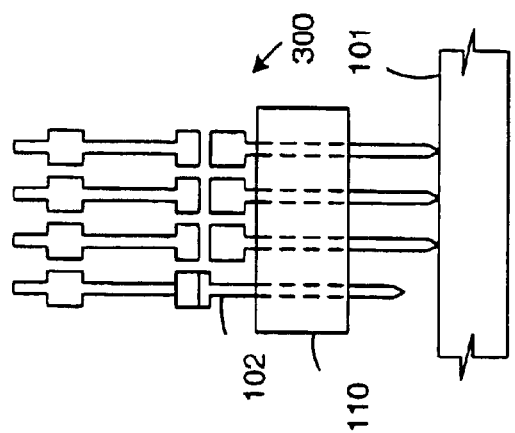
FIGS. 4G, 4H, and 4I show side views of another embodiment of pin-lifters constructed according to the invention.
Figure 4H:
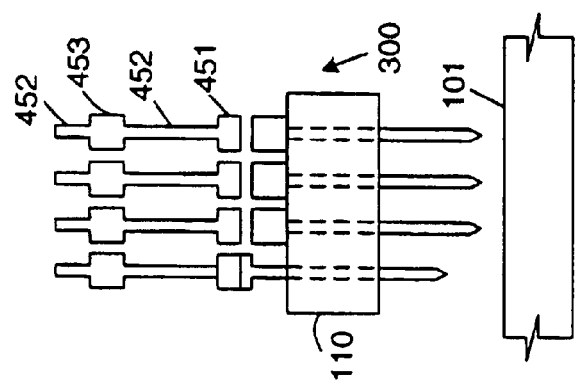
Figure 4G:
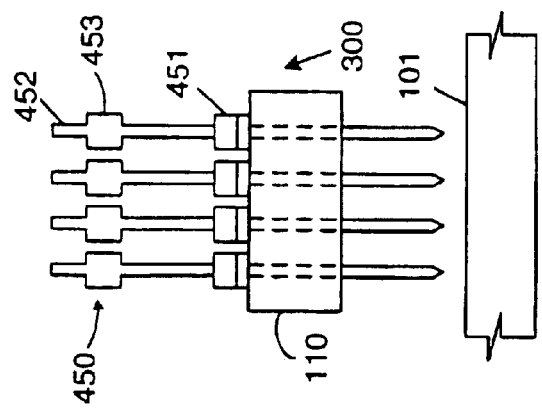

FIGS. 4G–4I illustrate another embodiment of a pin-lifter 450 constructed according to the invention. Rather than using electromagnetic forces, pin-lifter 450 uses suction to lift pins out of the printhead. Each pin-lifter 450 includes (1) a cylindrical cap 451 configured to partially cover a pin head, (2) a suction tube 452, and (3) a control valve 453. Normally, one pin-lifter 450 would be provided for every aperture in the printhead. Initially, the pin-lifters 450 are lowered so that the caps 451 cover their respective pins as shown in FIG. 4G. Thereafter, suction is selectively applied and the pin-lifters 451 are raised to selectively lift one or more pins out of the printhead as shown in FIG. 4H. FIG. 4I shows a printing in which the pin-lifters 450 prevent the pins in one row of the printhead from contacting the substrate 101. Normally, suction would be applied to all of the suction tubes 452 and the control valves 453 determine whether the suction will be applied to any particular pin head. It will be appreciated that pin-lifter 450 is representative of a variety of pin-lifters that can be constructed in accordance with the invention that use suction to lift pins out of a printhead. For example, other pin-lifters that use suction may not include a cap 451 for covering the pin head. It will further be appreciated that other types of mechanical pin-lifters may be constructed according to the invention. For example, instead of suction, small grippers could be used to selectively raise pins out of the printhead.

Figure 4J:
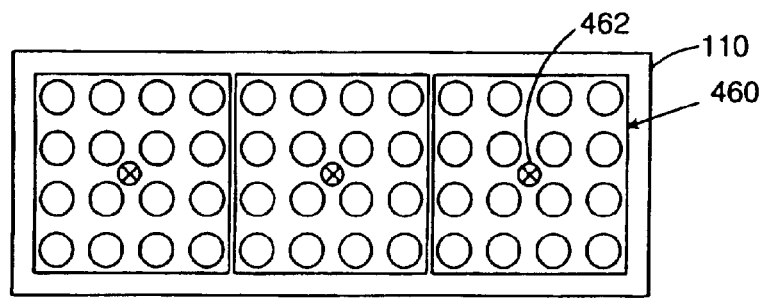
FIG. 4J shows a top view of another pin-lifter constructed according to the invention configured with a 48-pin printhead.
Figure 4K:
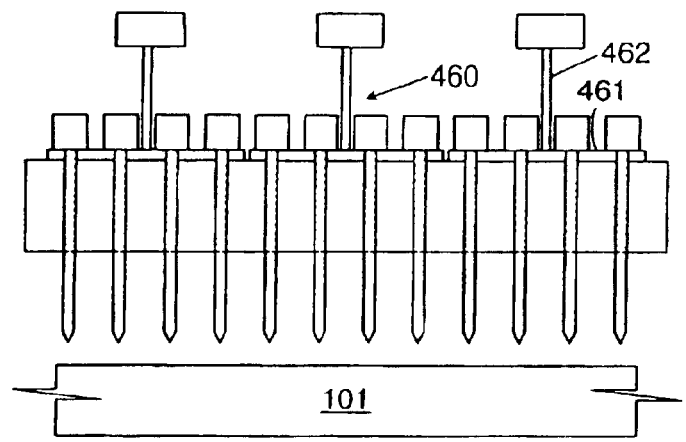
FIG. 4K shows a side view of the pin-lifters shown in FIG. 4J disposed over a substrate.
Figure 4L:
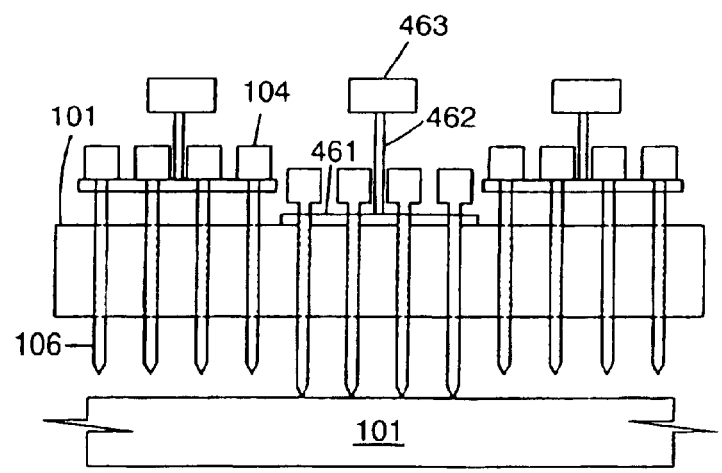
FIG. 4L shows a side view of the pin-lifters shown in FIG. 4K during a printing in which two of the pin-lifters prevent 32 pins from contacting the substrate.

FIGS. 4J, 4K, and 4L illustrate yet another embodiment of a mechanical pin-lifter 460 constructed according to the invention. FIGS. 4J and 4K show top and side views, respectively, of three pin-lifters 460 disposed over a 48 aperture printhead 110. FIG. 4L shows a printing during which only 16 of the 48 pins mounted in the printhead contact the substrate 101 because two of the pin-lifters 460 have prevented 32 pins from contacting the substrate 101 (i.e., each of the two pin-lifters 460 prevented 16 pins from contacting the substrate).

Pin-lifter 460 includes a plate 461, a rod 462, and a plate-lifter 463. In the illustrated embodiment, each plate 461 defines 16 apertures, and each plate 461 is disposed so that its 16 apertures are coaxially disposed over 16 corresponding apertures in the printhead 110. The apertures in the plate 461 are sized similarly to the apertures in the printhead 110 (i.e., the diameter of an aperture in the plate 461 is slightly larger than the outer diameter of a needle 106 and is smaller than the outer diameter of a pin head 104). The plates are disposed between the upper surface of the printhead 110 and the lower surface of the pin heads. The pin head 104 of each pin mounted in printhead 110 rests on one of the plates 461, and the needle 106 of each pin extends through two coaxial apertures defined by the plate and the printhead.

One end of rod 462 is attached to the center of plate 461 and the other end of rod 462 is attached to plate-lifter 463. Plate-lifter 463, which can be implemented for example using a solenoid or pneumatic actuator, can raise and lower the rod 462 which in turn raises or lowers plate 461 between a resting position and a lifted position. In the resting position, the plate 461 rests on the upper surface of printhead 110. FIG. 4K shows all three plates 461 disposed in the resting position. In the lifted position, the plate 461 is disposed above the printhead 110 and all pins mounted in the plate (i.e., all pins with needles that extend through an aperture of the plate) are corresponding lifted partially out of the printhead. FIG. 4L shows (1) the plate of the center pin-lifter 460 in the resting position and (2) the plates of the two pin-lifters 460 at the left and right ends of the printhead 110 in the lifted position. Each pin-lifter 460 can (1) prevent all pins mounted in its plate from contacting the substrate during a printing by placing its plate in the lifted position or (2) allow all pins mounted in its plate to contact the substrate during a printing by placing its plate in the resting position.

Plate 461 may be fabricated, for example, from metal or plastic material, such as nylon or acetal. It will be appreciated that plates of pin-lifter 460 can be configured to hold different numbers of pins. Normally the plates would be disposed so that every aperture in the printhead is coaxially disposed beneath an aperture defined by one of the plates. In this fashion, one or more pin-lifters 460 may be used to control the position of every pin in the printhead.

Although pin-lifter 460 is shown as including a rod 462 that connects the plate-lifter 463 to the plate 461, it will be appreciated that numerous mechanical arrangements could be used other than rod 462 for mechanically coupling the plate 461 to the plate-lifter 463. Also, plate-lifter 463 could be implemented using a variety of actuators. One advantage of pin-lifter 460 is that plate lifter 463 can lift pins more efficiently than direct electromagnetic pin-lifters that lift a pin across an air gap (e.g., pin-lifter 420). For example, when plate-lifter 463 is implemented as a solenoid, less current is required to lift plate 461 and all pins mounted therein than would normally be required by pin-lifter 420 (FIG. 4B) for attracting a single pin across the air gap.

As discussed above in connection with the electromagnetic pin-lifters 420 (FIG. 4A), 430 (FIG. 4E), 440 (FIG. 4F), application of electric current to the coil of a pin-lifter lifts one or more pins out of the printhead. Correspondingly, cessation of the electric current releases the previously lifted pins and allows them to fall back into a printing position within the printhead. Similarly, cessation of suction or mechanical gripping force will allow pins lifted by a mechanical pin-lifter (e.g., pin-lifter 450) to drop back into a printing position within the printhead. Since dropping a pin into the printhead may cause some of the liquid target material to leak out of the pin, it may be advantageous to reduce the impact caused when a pin-lifter releases a pin and allows that pin to drop back into the printhead.

One method according to the invention for reducing this impact is to provide a resilient material between the upper metallic surface of the printhead and the bottom of the pin heads (which normally rest of the printhead's upper surface). When no resilient material is so positioned, dropping a pin into an aperture of a printhead causes the metallic pin head to fall onto, and be stopped by, the upper metallic surface of the printhead. This metal-to-metal collision (i.e., the collision of the pin head with the upper surface of the printhead), causes the pin to experience a relatively sudden deceleration and may result in some of the liquid target material leaking out of the pin. However, if a pin is dropped into an aperture of a printhead while a resilient material is disposed between the upper surface of the printhead and the pin head, then the metallic pin head will fall onto the resilient material instead of the metallic upper surface of the printhead. The presence of the resilient material thereby (1) avoids the metal-to-metal collision; (2) reduces the deceleration experienced by the pin; and (3) may reduce the amount of liquid target material that leaks out of the pin as a result of being dropped into an aperture of a printhead.

Figure 5A:
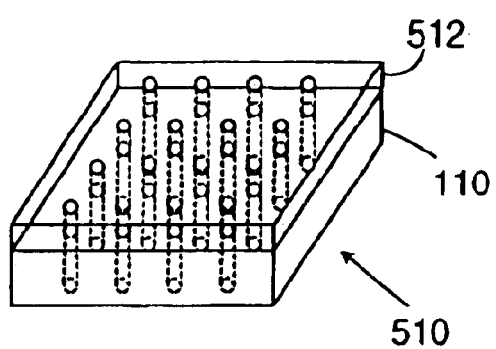
FIG. 5A shows a perspective view of a printhead constructed in accordance with the invention.

FIG. 5A shows a printhead 510 constructed according to the invention so as to position a resilient or soft material between the upper metallic surface of a printhead and the pin heads. Printhead 510 includes a sheet of resilient material (e.g., rubber) 512 disposed over a prior art printhead 110. Sheet 512 defines a plurality of apertures corresponding to the apertures in printhead 110 and is disposed so that the apertures of sheet 512 are coaxial with the apertures of printhead 110. If a pin is dropped into one of the apertures of printhead 510, the pin head will contact the resilient sheet 512 rather than the upper metallic surface of printhead 110 and thereby experience a reduced deceleration.

Figure 5B:
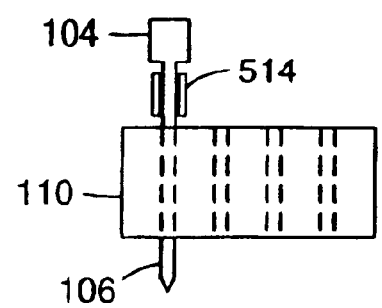
FIG. 5B shows a spring disposed between a printhead and a pin head in accordance with the invention.

Another method of positioning a resilient material between the pin head and the upper metallic surface of the printhead is to position a spring (e.g., a coil spring or an annular disk of resilient material) around the needle of the pin. FIG. 5B shows such a spring 514 positioned around the needle 106 between the pin head 104 and the upper metallic surface of a printhead. If the pin 102 is dropped into an aperture of printhead 110 when the spring 514 is positioned as shown in FIG. 5B, the spring 514 will cushion the fall of pin 102, or reduce the deceleration experienced by the pin.

Another method of reducing the amount of liquid target material that leaks out of a pin when the pin is released by a pin-lifter, is to lower the pin lifter prior to releasing the pin. For example, pin-lifter 420 (FIG. 4A) could be lowered to place the bottom of the pin head into, or nearly into, contact with the upper surface of the printhead before the pin-lifter releases the pin. One advantage of pin-lifter 460 (FIG. 4J) is that it can lower the plate 461 slowly and thereby avoid suddenly decelerating the pins mounted therein. Also, the plate 461 can be fabricated from a resilient material so as to reduce the deceleration experienced by pins when they are lowered by the pin-lifter 460.

Figure 6A:
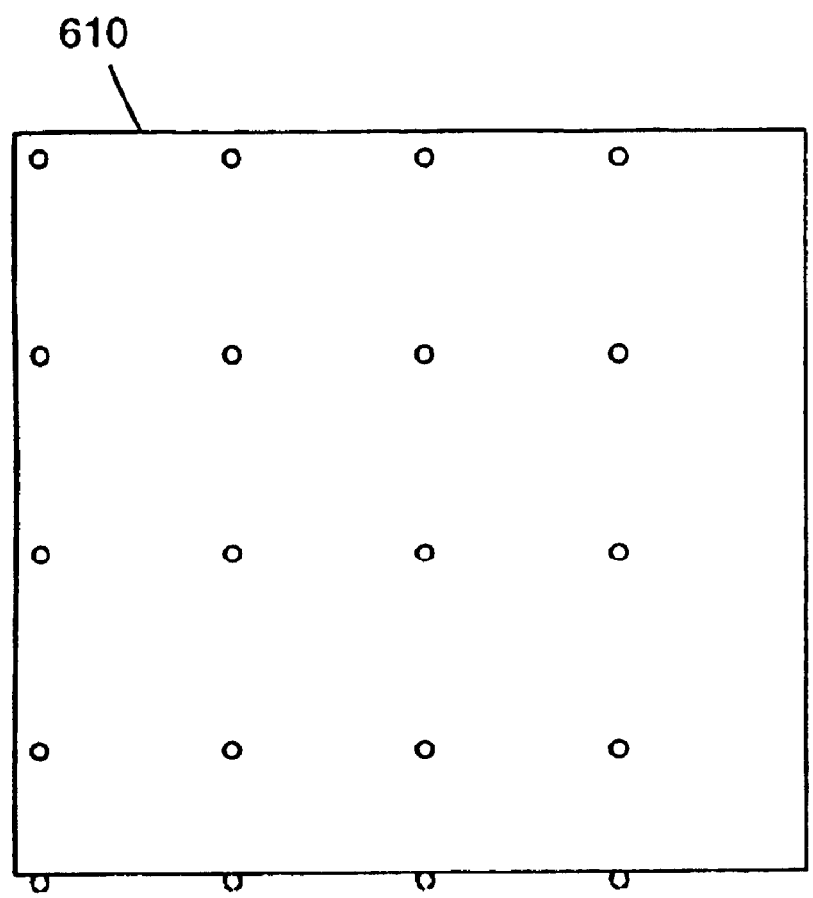
FIGS. 6A, 6B, 6C, and 6D illustrate how pin-lifters constructed according to the invention may be used in accordance with the invention to facilitate production of compact microarrays.
Figure 6A:
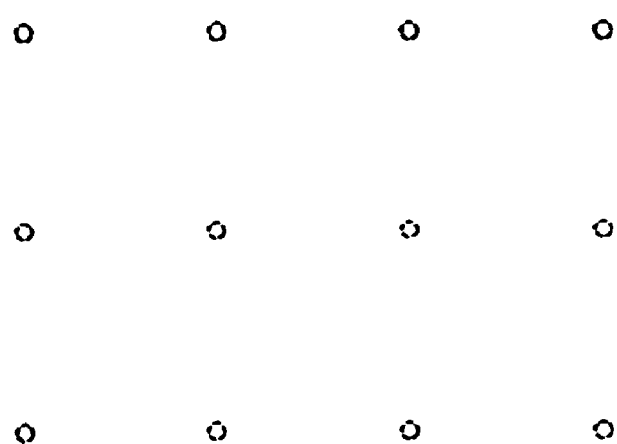

Some advantageous methods of using pin-lifters according to the invention will now be described. Pin-lifters constructed according to the invention are useful for, among other things, increasing the rate of production of compact microarrays. FIGS. 6A, 6B, 6C, and 6D illustrate one method of using pin-lifters according to the invention to increase the rate of production of a compact microarray. FIG. 6A illustrates the location of a 32 pin printhead relative to an active area 610 of a microarray during a single printing. Active area 610 is the area within which all spots of the microarray are to be deposited. In FIG. 6A, each of the 32 open circles represents the location of a pin that is held by a 32 pin printhead. The 16 circles drawn with solid lines represent pins that are allowed to contact the microarray's substrate during this printing, and the 16 circles drawn with dashed lines represent pins that have been lifted by one or more pin-lifters constructed according to the invention and thereby prevented from contacting the microarray's substrate during the printing. So although 32 pins are mounted in the printhead, the printing illustrated in FIG. 6A results in only 16 spots being deposited onto the microarray, and the action of the pin-lifter prevents all pins that are not disposed over the active area 610 from contacting the substrate.

Figure 6B:
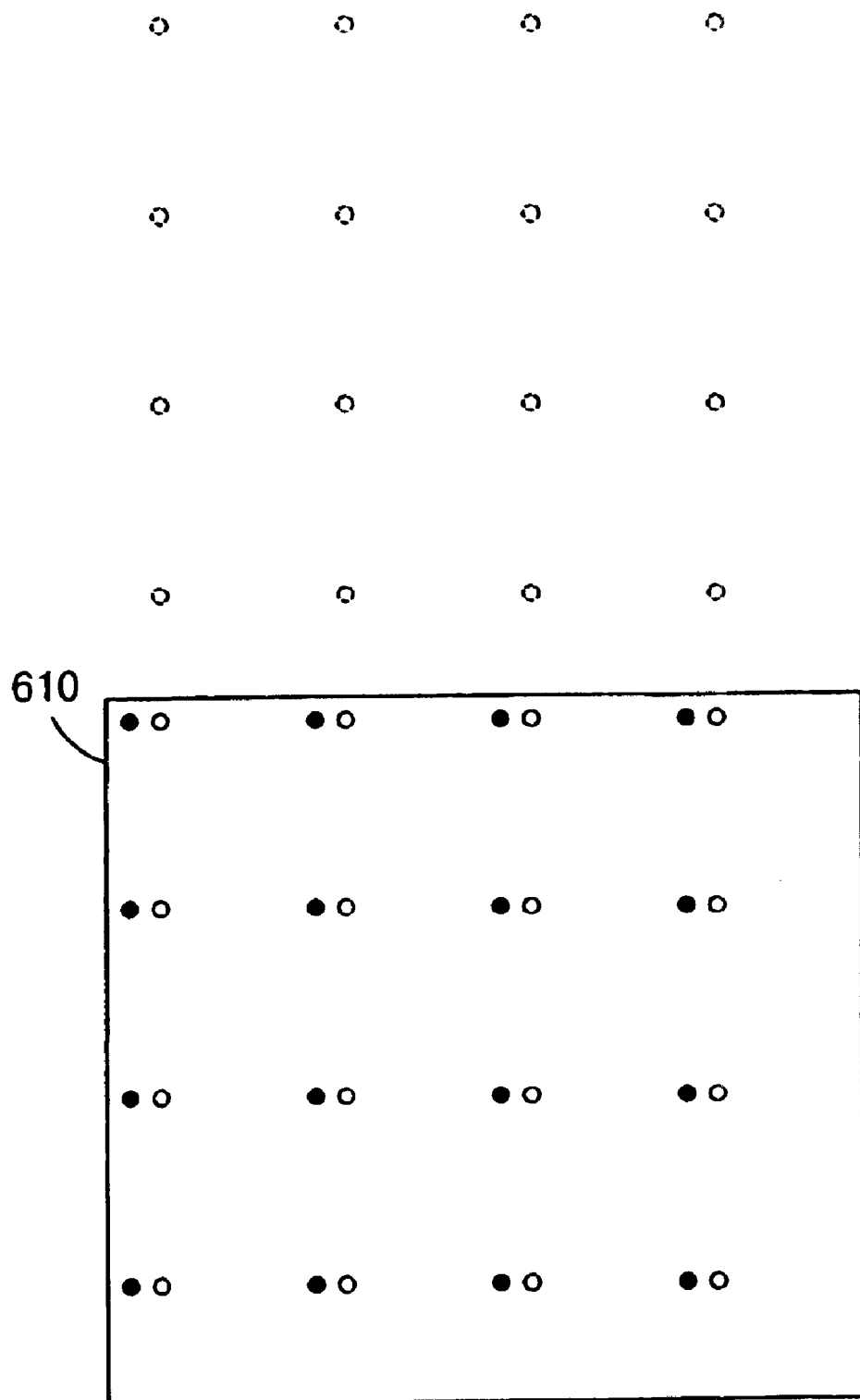

FIG. 6B illustrates the location of the 32 pin printhead relative to the active area 610 during another printing. In FIG. 6B, (1) the solid black circles represent spots that were deposited during the printing illustrated in FIG. 6A, (2) the open circles drawn with solid lines represent pins that are allowed to contact the microarray's substrate during the printing, and (3) the open circles drawn with dashed lines represent pins that have been lifted by one or more pin-lifters constructed according to the invention and thereby prevented from contacting the microarray's substrate during the printing. The pins that were not used (i.e., the pins that were lifted by the pin-lifter and thereby not allowed to contact the microarray's substrate) during the printing illustrated in FIG. 6A are used (i.e., they are allowed to contact the substrate) during the printing illustrated in FIG. 6B. Similarly, the pins that were used during the printing illustrated in FIG. 6A are not used during the printing illustrated in FIG. 6B.

Figure 6C:
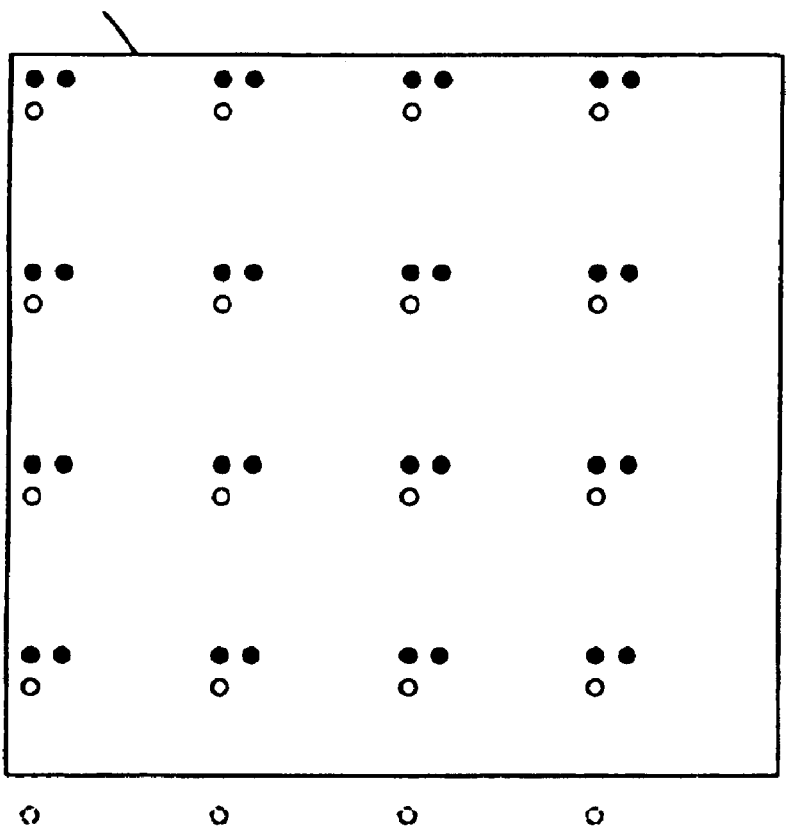
Figure 6C:
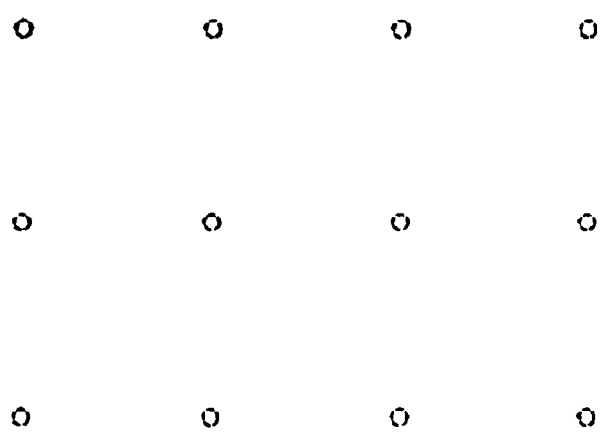
Figure 6D:
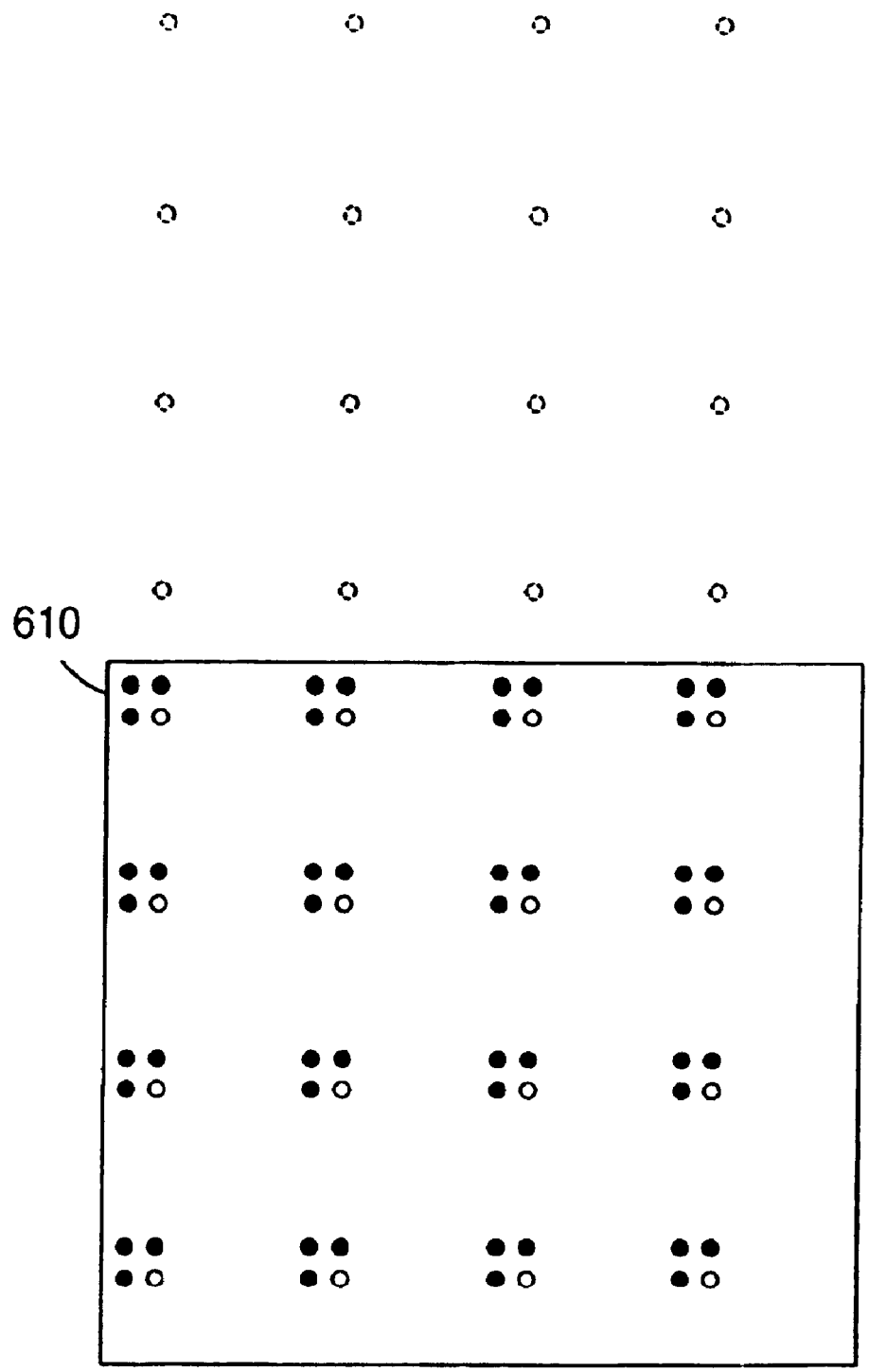

FIG. 6C illustrates the location of the 32 pin printhead relative to the active area 610 during yet another printing. In FIG. 6C, (1) the solid black circles represent spots that were deposited during the printings illustrated in FIGS. 6A and 6B, (2) the open circles drawn with solid lines represent pins that are allowed to contact the microarray's substrate during the printing, and (3) the open circles drawn with dashed lines represent pins that have been lifted by one or more pin-lifters constructed according to the invention and thereby prevented from contacting the microarray's substrate during the printing. FIG. 6D illustrates the location of the 32 pin printhead relative to the active area 610 during still another printing. In FIG. 6D, (1) the solid black circles represent spots that were deposited during the printings illustrated in FIGS. 6A, 6B, and 6C, (2) the open circles drawn with solid lines represent pins that are allowed to contact the microarray's substrate during the printing, and (3) the open circles drawn with dashed lines represent pins that have been lifted by one or more pin-lifters constructed according to the invention and thereby prevented from contacting the microarray's substrate during the printing. The active area 610 may be filled in with all desired spots by performing a series of printings and by using the pin-lifter during each printing to prevent all pins that are not disposed over the active area from contacting the microarray's substrate.

Use of a pin-lifter constructed according to the invention does not reduce the number of printings required to fabricate any given microarray. However, use of a pin-lifter constructed according to the invention increases the rate of production of compact microarrays because it reduces the required number of washing, drying, and re-dipping steps, as well as the long robotic actuator traverses associated with the washing, drying, and re-dipping steps. For example, in the method illustrated in FIGS. 6A–6D, although 32 pins are mounted in the printhead, only 16 of the pins are allowed to contact the microarray's substrate during any given printing. Therefore, a printhead carrying only 16 pins could produce an identical microarray using the same number of printings (i.e., assuming all 16 pins are allowed to contact the microarray's substrate during each printing). However, if only 16 pins were mounted in the printhead (and all 16 pins were used during every printing), those pins would exhaust their supply of target material twice as quickly as the 32 pins used as described in connection with FIGS. 6A–6D. Therefore, if only 16 pins were used, those pins would have to be washed, dried, and re-dipped into the reservoir of target material twice as often. Since washing and drying steps are relatively time consuming as compared with other steps in microarray fabrication, decreasing the number of required washing and drying steps significantly increases the rate of production.

Figure 7A:
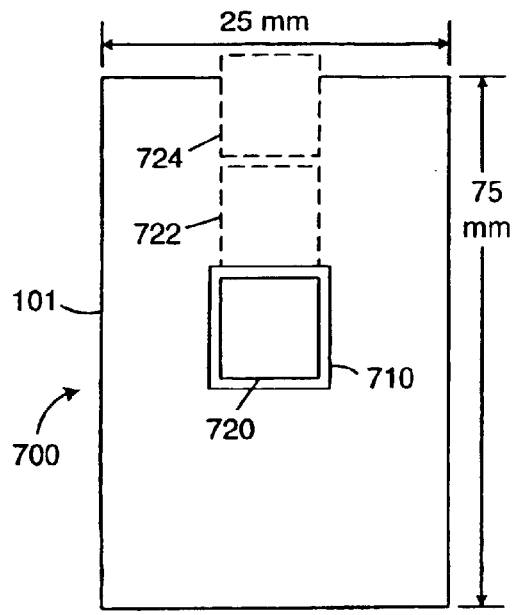
FIGS. 7A, 7B, and 7C illustrate how pin-lifters constructed according to the invention may be used in accordance with the invention to facilitate production of compact microarrays.
Figure 7B:
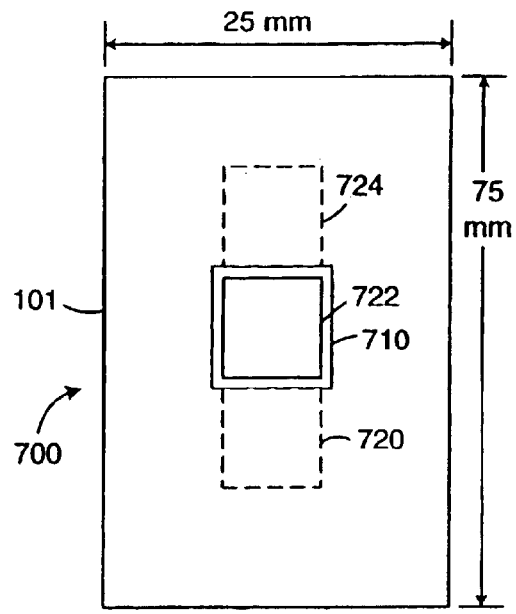
Figure 7C:
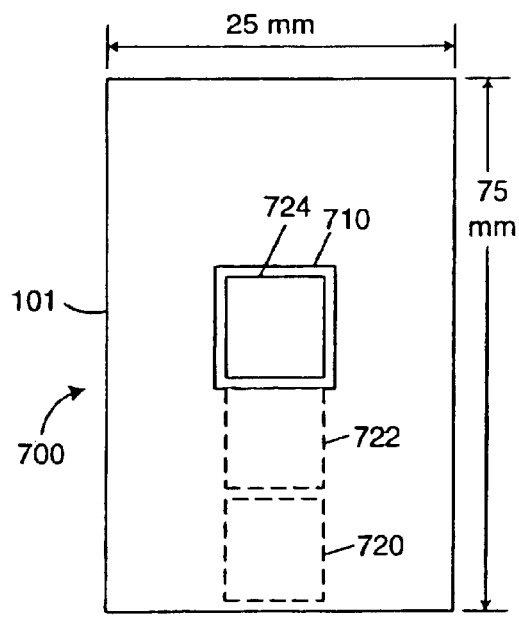

FIGS. 7A, 7B, and 7C show another example of using a pin-lifter according to the invention to increase the rate of production of compact microarrays. FIGS. 7A, 7B, and 7C show a microarray 700 that is being constructed according to the invention. It is desired to place all the spots of target material of microarray 700 within a relatively small, compact, active area 710 located near the center of substrate 101. The three squares 720, 722, 724 shown in FIGS. 7A, 7B, and 7C represent the footprint of the printhead that is used to fabricate microarray 700. As shown, the printhead's footprint is significantly larger than the active area 710. Accordingly, use of prior art manufacturing techniques would require that the printhead be less than fully populated with pins during the fabrication of microarray 700. However, use of a pin-lifter constructed according to the invention allows the printhead to be fully populated during fabrication of microarray 700. FIGS. 7A, 7B, and 7C illustrate the location of the printhead during three separate printings. During each of the printings, a pin-lifter constructed according to the invention (1) prevents all pins that are not disposed over the active area 720 from contacting the substrate 101 and (2) allows pins that are disposed over the active area 720 to contact the substrate and thereby form spots of the microarray 700. For example, during the printing illustrated in FIG. 7B, the pin-lifter permits the pins located within portion 722 of the printhead's footprint to contact the substrate 101 and the pin-lifter prevents the pins located within the portions 720 and 724 of the footprint from contacting the substrate.

As described above, one advantageous use of pin-lifters constructed according to the invention is for increasing the rate of production of compact microarrays. However, it will be appreciated that pin-lifters constructed according to the invention have other uses as well. For example, in the prior art, 96-well plates could only be used with either (1) a 9.0 mm center spaced printhead or (2) a 4.5 mm center spaced printhead in which only one out of every four apertures carried a pin (i.e., three out of every four apertures had to be empty) and in which all adjacent mounted pins were spaced apart from one another by 9.0 mm. If a fully populated 4.5 mm center spaced printhead were dipped into a 96-well plate, some of the pins would be damaged. However, pin-lifters constructed according to the invention provide a convenient way to facilitate use of fully populated 4.5 mm center-spaced printheads with either 96-well or 384-well plates. When it is desired to use a 384-well plate, the pin-lifters can remain inactive allowing all pins to rest in the printhead. However, when it is desired to use a 96-well plate, the pin-lifters can raise three out of every four pins partially out of the printhead so that all adjacent pins resting in the printhead are spaced apart from one another by 9.0 mm. In this fashion, pin-lifters constructed according to the invention can be advantageously used to effectively convert a 4.5 mm center-spaced printhead into a 9.0 mm center-spaced printhead without requiring manual removal of any pins. More generally, spotting instruments constructed according to the invention can operate in both high density and low density modes, and can easily toggle back and forth between the two modes as desired. In the low density mode, pin-lifters are used to lift selected pins out of the printhead, and in the high density mode, the pin-lifters can remain inactive. When it is desired to use a pin-lifter to prevent a pin from being dipped into a reservoir while some other pin is being dipped, it may be necessary to lift the pin further out of the printhead than is typically required to prevent a pin from printing (e.g., it may be advantageous for the pin lifter to be able to lift pins by about 5 millimeters out of the printhead). It will further be appreciated that in addition to the above-described high and low density modes, it may be advantageous to prevent arbitrary subsets of pins from being dipped into a reservoir while other pins in the printhead are being dipped into a reservoir.

Another advantage of pin-lifters constructed according to the invention is that they provide a high degree of flexibility when fabricating microarrays. For example, whenever two or more pins mounted in a printhead are simultaneously used to print spots on a microarray, the spots from those pins will be spaced apart by a distance that is determined by the configuration of the printhead. However, pin-lifters can be used to traverse this limitation caused by the geometry of the printhead. For example, pin-lifters can be used to prevent all but a single selected pin from contacting the substrate during any printing. This allows spots from any pin to be placed at any arbitrary desired location on the substrate. This may be useful for example for producing microarrays in which each group of spots corresponds to the location of the well from which the target material for those spots was drawn. For example, it may be desirable to use a 96-well plate to produce a microarray having 96 groups of spots, with each group corresponding to one of the wells (i.e., all the spots in each group are made by liquid target material drawn from a corresponding one of the wells). In the prior art, if such a microarray were made using a fully populated 96 aperture printhead, each group of spots could be no larger than the space between adjacent pins, and this may have imposed an undesirable upper limit on the number of spots in each group. However, if pin-lifters are used to prevent all but one pin from contacting the substrate during every printing, then the only limit on the size of (or the number of spots within) each group of such a microarray is determined by the size of the substrate and no limit is imposed by the spacing between apertures of the printhead.

If a pin-lifter is actuated but fails to lift its corresponding pin out of the printhead, the microarray being produced may be adversely affected. For example, one or more spots of target material may be deposited at undesired or unknown locations on the microarray substrate. Other deleterious effects, such as causing damage to pins, may also result. Similar problems can occur if a pin-lifter prematurely drops a pin back into the printhead. Accordingly, it may be advantageous to provide pin-lifters constructed according to the invention with a feedback mechanism for detecting whether the pin-lifter has actually lifted a pin.

Figure 8A:
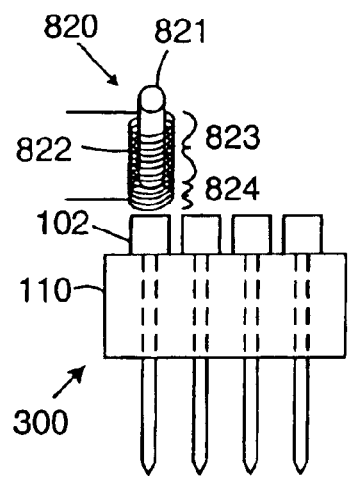
FIG. 8A shows a pin-lifter-sensor constructed according to the invention disposed over a 16-pin printhead.
Figure 8B:
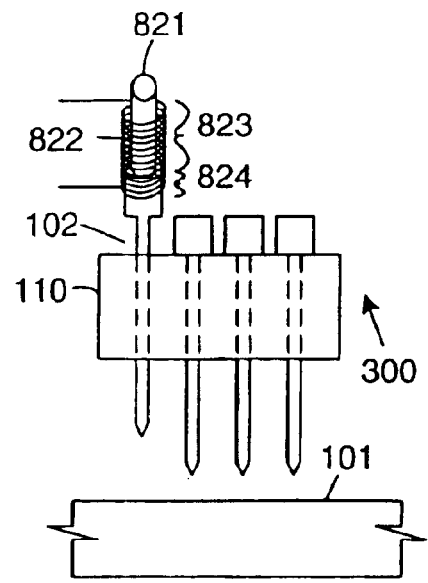
FIG. 8B shows the pin-lifter-sensor shown in FIG. 8A lifting four pins partially out of the printhead.

FIGS. 8A and 8B illustrate a pin-lifter-sensor 820 constructed according to the invention. Like pin-lifter 420 (FIG. 4A), pin-lifter-sensor 820 includes a core 821 of ferromagnetic material and a coil 822 of wire. Coil 822 is a continuous coil of wire. An upper portion 823 of the coil 822 is wound around the core 821 and a lower portion 824 of the coil 822 extends below the core 821. As shown in FIG. 8A, when the pin-lifter-sensor 820 is inactive and the pin below it is resting in the printhead, then the lower portion 824 is filled with air (i.e., as in an air filled inductor). However, when the pin-lifter-sensor 820 is actuated and thereby attracts the pin below it across the air gap and brings the pin head into contact with the bottom of core 821, then the lower portion 824 is effectively wrapped around the metallic pin head, or is filled with metal (i.e., as in an iron core inductor). The presence or absence of a pin head within the lower portion 824 significantly affects the inductance of coil 822. That is, when the pin is in contact with core 821 so that the lower portion 824 is filled with the metallic pin head (as shown in FIG. 8B), the inductance of winding 822 is significantly higher than when the pin head is resting in the printhead and the lower portion 824 is air filled. This change in inductance permits pin-lifter-sensor 820 to act as a sensor for determining whether a pin has been lifted.

Spotting instruments constructed according to the invention may monitor the inductance of the pin-lifter-sensors to determine whether selected pins have actually been lifted out of the printhead. If at any time it is detected that a pin that should be lifted has not in fact been lifted, or has fallen back into the printhead, the appropriate pin-lifter-sensor may be reactivated prior to proceeding with fabrication of the microarray. If presence of a lifted pin is not detected even after reactivation of the pin-lifter-sensor, it is possible that the pin-lifter-sensor is inoperative and needs to be repaired. Alternatively, it is possible that no pin has been mounted in the appropriate aperture of the printhead and a pin should be added before proceeding with fabrication of the microarray.

Co-pending U.S. patent application Ser. No. 09/527,892, entitled METHOD AND APPARATUS FOR PIN DETECTION IN MICROARRAY SPOTTING INSTRUMENTS describes several sensors that may be used to detect the presence of pins within a printhead. Spotting instruments constructed according to the invention may use those sensors in conjunction with the pin-lifters or pin-lifter-sensors of the present invention to facilitate production of microarrays. For example, if the sensors detect that no pin is mounted within a particular aperture of the printhead, then the spotting instrument will know that the pin-lifter for that aperture need not be activated. Such sensors could also be used to detect which, if any, pins are mounted within the group of apertures controlled by a pin-lifter 460 (FIG. 4L).

Figure 9:
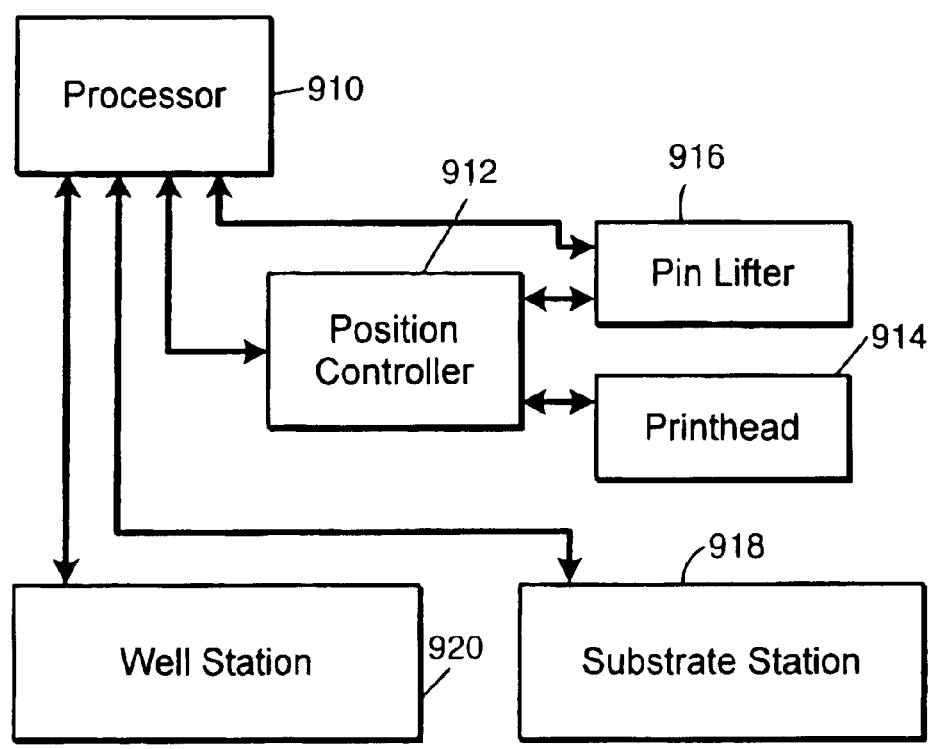
FIG. 9 shows a block diagram of a spotting instrument constructed in accordance with the invention.

FIG. 9 shows a block diagram of a spotting instrument 900 constructed according to the invention. Spotting instrument 900 includes a processor 910, a position controller 912, a printhead 914, one or more pin-lifters or pin-lifter-sensors 916, a base 918 for holding one or more microarray substrates, and a base 920 for holding one or more reservoirs of liquid target material (e.g., a 96-well plate). Although not illustrated, it will be appreciated that spotting instrument 900 additionally includes a pin washer and a dryer. The position controller 912 (e.g., one or more robotic manipulators) moves the printhead 914 and pin-lifters 916 to locations selected by the processor 910. Normally, the printhead 914 and pin-lifters 916 are moved together, however, it is also desirable to provide independent control over movement of the printhead 914 and the pin-lifters 916. For example, it may be desirable to be able to move the pin-lifters 916 to a position that is removed from printhead 914 to facilitate loading pins into the printhead and to thereafter move the pin-lifters 916 over the printhead 914 to a position where they can selectively lift pins out of the printhead. Processor 910 controls the pin-lifters 916 during fabrication of microarrays to selectively prevent pins in the printhead from contacting the substrate during selected printings. Although not shown, the instrument 900 may also include pin sensors of the type described in the above-referenced U.S. patent application Ser. No. 09/527,892. Such sensors would also be coupled to processor 910.

Since certain changes may be made in the above apparatus without departing from the scope of the invention herein involved, it is intended that all matter contained in the above description or shown in the accompanying drawing shall be interpreted in an illustrative and not a limiting sense. By way of example, spotting instruments have been discussed above that use the following method to selectively prevent some pins from contacting the substrate during a printing: (1) position the printhead over a substrate; (2) use one or more pin lifters to lift some of the pins partially out of the printhead; and (3) lower the printhead thereby allowing the pins that have not been lifted to contact the substrate. However, other methods of using pin lifters to prevent some pins from contacting the substrate are embraced by the invention. For example, as one alternative, pin lifters could be used to lift all pins partially out of a printhead, the printhead could then be positioned over a substrate close enough to the substrate so that any pins released by the pin lifters would contact the substrate, and then the pin lifters could release a selected set of pins and thereby allow those released pins to contact the substrate. Thereafter, the pin lifters could lift (or re-lift) all the released pins and then the printhead could be moved to a new location. It will be appreciated that other variations on the disclosed embodiments and methods are also embraced by the invention.

What is claimed is:

1. A method of producing a microarray, including:

(A) mounting a plurality of pins in a printhead;

(B) moving the printhead to a first location over a substrate so that a first subset of two or more of the pins is disposed over an active area of the substrate and a second subset of two or more of the pins is not disposed over the active area;

(C) lowering the printhead and thereby allowing the first subset of pins to contact the substrate while preventing the second subset of pins from contacting the substrate;

(D) moving the printhead to a second location over the substrate so that the first subset of pins is not disposed over the active area and the second subset of pins is disposed over the active area; and (E) lowering the printhead and thereby allowing the second subset of pins to contact the substrate while preventing the first subset of pins from contacting the substrate.

2. A method according to claim 1, wherein preventing the second subset of pins from contacting the substrate comprises lifting the second subset of pins at least partially out of the printhead.

3. A method according to claim 2, wherein lifting the second subset of pins comprises using an electromagnetic force.

4. A method according to claim 3, wherein using an electromagnetic force comprises using the electromagnetic force to attract the pins across an air gap between the pins and one or more electromagnets.

5. A method according to claim 2, wherein lifting the second subset of pins comprises using suction.

6. A method according to claim 2, wherein lifting the second subset of pins comprises using a mechanical lifter.

7. A method according to claim 2, wherein lifting the second subset of pins comprises using a pneumatic actuator.

8. A method according to claim 2, wherein lifting the second subset of pins comprises lifting a support on which the pins rest.

9. A method according to claim 1, wherein the second subset of pins comprises a row of pins.

10. A method according to claim 1, wherein the second subset of pins comprises a rectangular group of pins.

11. A method according to claim 1, wherein lowering the printhead and thereby allowing the first subset of pins to contact the substrate while preventing the second subset of pins from contacting the substrate comprises lowering the printhead by an amount that is greater than required to allow the first subset of pins to contact the substrate and further comprises lifting the second subset of pins by an amount sufficient to prevent the second subset of pins from contacting the substrate.

12. A method according to claim 1, further comprising dipping the pins in a reservoir of liquid material.

13. A method according to claim 12, wherein dipping the pins comprises dipping each of the pins into a separate well of liquid material.

14. A method of producing a microarray, including:

(A) mounting a plurality of pins in a printhead;

(B) moving the printhead to a first location over a substrate so that a first subset of two or more of the pins are disposed over an active area of the substrate and a second subset of two or more of the pins are not disposed over the active area;

(C) lowering the printhead and thereby allowing the first subset of pins to contact the substrate while preventing the second subset of pins from contacting the substrate;

(D) moving the printhead to a second location over a substrate so that a third subset of two or more of the pins are disposed over an active area of the substrate and a fourth subset of two or more of the pins are not disposed over the active area; and (E) lowering the printhead and thereby allowing the third subset of pins to contact the substrate while preventing the fourth subset of pins from contacting the substrate.

15. A method according to claim 14, wherein the third subset of pins is identical to the second subset of pins, and wherein the fourth subset of pins is identical to the first subset of pins.

16. A method according to claim 14, wherein preventing the second subset of pins from contacting the substrate comprises lifting the second subset of pins at least partially out of the printhead.

17. A method according to claim 16, wherein lifting the second subset of pins comprises using an electromagnetic force.

18. A method according to claim 17, wherein using an electromagnetic force comprises using the electromagnetic force to attract the pins across an air gap between the pins and one or more electromagnets.

19. A method according to claim 16, wherein lifting the second subset of pins comprises using suction.

20. A method according to claim 16, wherein lifting the second subset of pins comprises using a mechanical lifter.

21. A method according to claim 16, wherein lifting the second subset of pins comprises using a pneumatic actuator.

22. A method according to claim 16, wherein lifting the second subset of pins comprises lifting a support on which the pins rest.

23. A method according to claim 14, wherein the second subset of pins comprises a row of pins.

24. A method according to claim 14, wherein the second subset of pins comprises a rectangular group of pins.

25. A method according to claim 14, wherein lowering the printhead and thereby allowing the first subset of pins to contact the substrate while preventing the second subset of pins from contacting the substrate comprises lowering the printhead by an amount that is greater than required to allow the first subset of pins to contact the substrate and further comprises lifting the second subset of pins by an amount sufficient to prevent the second subset of pins from contacting the substrate.

26. A method according to claim 14, further comprising dipping the pins in a reservoir of liquid material.

27. A method according to claim 26, wherein dipping the pins comprises dipping each of the pins into a separate well of liquid material.

* * * * *